US012037663B2

(12) United States Patent
Duocastella Codina et al.

(10) Patent No.: US 12,037,663 B2
(45) Date of Patent: Jul. 16, 2024

(54) BETA-PHASE TITANIUM AND TUNGSTEN ALLOY

(71) Applicant: LIFE VASCULAR DEVICES BIOTECH, S.L., Sant Vicenç Dels Horts (ES)

(72) Inventors: Luis Duocastella Codina, Sant Vicenç Dels Horts (ES); Isabel Pérez Serranos, Castellbisbal (ES); Arnau Vidal Parreu, Sant Feliu de Llobregat (ES)

(*) Notice: Subject to any disclaimer, the term of this patent is extended or adjusted under 35 U.S.C. 154(b) by 208 days.

(21) Appl. No.: 17/058,050

(22) PCT Filed: May 27, 2019

(86) PCT No.: PCT/EP2019/063613
§ 371 (c)(1),
(2) Date: Nov. 23, 2020

(87) PCT Pub. No.: WO2019/228963
PCT Pub. Date: Dec. 5, 2019

(65) Prior Publication Data
US 2021/0198771 A1    Jul. 1, 2021

(30) Foreign Application Priority Data

May 28, 2018   (EP) .................................... 18382365

(51) Int. Cl.
*C22C 14/00*   (2006.01)
*A61L 31/02*   (2006.01)
(Continued)

(52) U.S. Cl.
CPC ............ *C22C 14/00* (2013.01); *A61L 31/022* (2013.01); *C21D 8/0226* (2013.01);
(Continued)

(58) Field of Classification Search
CPC ... A61L 31/022; C21D 8/0226; C21D 8/0236; C21D 9/46; C22C 1/02; C22C 14/00; C22F 1/183
(Continued)

(56) References Cited

U.S. PATENT DOCUMENTS

2005/0268746 A1*   12/2005   Abkowitz ............. A61L 31/022
                                                                148/421
2008/0029186 A1    2/2008   Abkowitz et al.
2014/0079583 A1*   3/2014   Abkowitz ........... C22C 32/0047
                                                                419/14

FOREIGN PATENT DOCUMENTS

JP           H09194968 A      7/1997

OTHER PUBLICATIONS

Microstructures and Grain Refinement of additive-manufactured Ti-xW alloys, Metallurgical and Materials Transactions A, vol. 48 A, 2017 pp. 3594-3605 (Year: 2017).*

(Continued)

*Primary Examiner* — Jie Yang
(74) *Attorney, Agent, or Firm* — Squire Patton Boggs (US) LLP

(57) ABSTRACT

The present invention relates to a beta titanium alloy comprising from 15% to 40% by weight of tungsten; and a balance amount of titanium up to 100% by weight; wherein the alloy comprises from 70% to 100% by volume of an equiaxed beta grain structure and to processes for its preparation. The invention also relates to an implantable medical device made of the beta titanium alloy.

3 Claims, 1 Drawing Sheet

(A)

(B)

(51) Int. Cl.
 *C21D 8/02* (2006.01)
 *C21D 9/46* (2006.01)
 *C22C 1/02* (2006.01)

(52) U.S. Cl.
 CPC ............ *C21D 8/0236* (2013.01); *C21D 9/46* (2013.01); *C22C 1/02* (2013.01)

(58) Field of Classification Search
 USPC ........................................................ 420/417
 See application file for complete search history.

(56) References Cited

OTHER PUBLICATIONS

International Search Report and Written Opinion mailed Jul. 24, 2019 for International Application No. PCT/EP2019/063613, 18 pages.
Standard Test Methods for Determining Average Grain Size according to ASTM E112, 13, 28 pages, Feb. 2014.
Standard Test Methods for Tension Testing of Metallic Materials according to ASTM E8/E8M, 16a, 30 pages, Sep. 2016.
European EN 10002-1 Metallic Materials—Tensile Testing—Part 1: Method of test at ambient temperature, ASTM E8M, 57 pages, Jul. 2001.
Bish, et al: "Quantitative Phase Analysis Using the Rietveld Method", J. Appl. Cryst. 1988, vol. 21, pp. 86-91.
Frary, et al: "Microstructure and mechanical properties of Ti/W and Ti-6A1-4V/W composites fabricated by powder metallurgy", Materials Science and Engineering 2003, vol. A344, pp. 103-112.

* cited by examiner

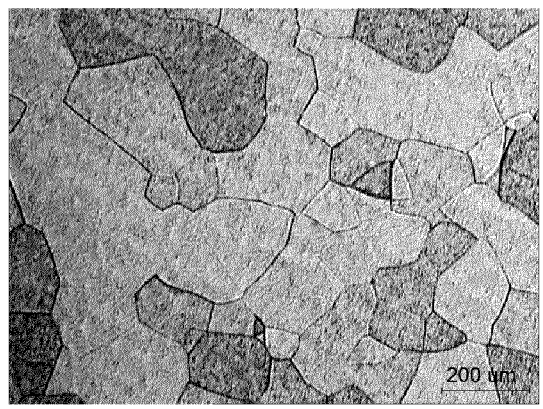 
(A)                                  (B)

BETA-PHASE TITANIUM AND TUNGSTEN ALLOY

CROSS-REFERENCE

This application is a 35 USC 371 national phase filing of PCT/EP2019/063613 filed on May 27, 2019, which claims the benefit and priority of European Patent Application EP18382365.7 filed on May 28, 2018, both applications are incorporated herein by reference in their entirety.

The present invention relates to titanium alloys containing tungsten. In particular, it relates to a new beta titanium alloy comprising from 15% to 40% by weight of tungsten; and a balance amount of titanium up to 100% by weight; wherein the alloy comprises from 70% to 100% by volume of an equiaxed beta grain structure. The invention also relates to an implantable medical device made of the beta titanium alloy containing tungsten.

BACKGROUND ART

Titanium (Ti) has been used for long in dentistry and medicine for implant purpose. During the years, not only the commercially pure Ti but also some alloys such as binary and ternary Ti alloys were used. Many metallic elements have been considered for making new titanium alloys for medical use. The key criteria for selecting alloying elements are having a high strength and high ductility. These properties can be achieved through the use of beta (β) phase titanium alloys. The beta phase of Titanium or Titanium allows refers to one of the two allotropic forms of titanium having a body-centered cubic structure usually found at high temperature. The beta phase provides a lower modulus and better fatigue resistance compared to the alpha (α) phase, normally found in Titanium at lower temperatures.

To stabilize the beta phase at low temperatures, 'beta stabilizer' alloying elements including niobium (Nb), molybdenum (Mo), tantalum (Ta), vanadium (V), chromium (Cr), manganese (Mn), cobalt (Co), nickel (Ni), and copper (Cu), zirconium (Zr) or tin (Sn) can be added. However, the main drawback of these alloys is the biocompatibility of the alloying elements.

Highly ductile and high strength biocompatible alloys are desired for medical applications, such as orthopaedic implants and impantable medical devices. Good ductility is desired both for being formable (malleable) enough to produce the final shape by metalworking and for possessing sufficient fracture resistance to deformation for medical applications.

It has been disclosed in the state of the art other biocompatible titanium alloying elements including amongst others tungsten. Titanium alloys containing tungsten have a strong wear resistant. However, tungsten is a heavy metal element that causes severe segregation problems when incorporated in the ingot melting industrial technology. In fact, the large difference in density between Titanium and tungsten in combination with the disparity between their melting points results in obtaining non-homogeneous alloys which compromise the mechanical properties of the resulting alloy.

Thus, there is a need to develop new titanium alloys containing tungsten having highly mechanical properties for being used in the medical field.

SUMMARY OF INVENTION

The inventors have found a beta titanium and tungsten alloy that have from 70% to 100% by volume of an equiaxed beta grain structure which is a metastable alloy that has a high strength and a high uniform ductility. In particular, the alloys of the present invention have the appropriate properties for being used in medical applications, for instance, as implantable medical device.

Furthermore, the inventors have also found that the beta titanium alloy of the present invention is a "strain-transformable" alloys showing a strain-transforming effects when the beta phase is in metastable state (i.e. quenched from beta region T around beta transus temperature). Without being bound by any theory, it seems that the deformation mechanisms of the strain-transforming effects can be featured by stress-induced martensitic transformation (SIM), mechanical twinning and dislocation slip. These mechanisms can be triggered simultaneously during the mechanical deformation. The strain transforming effects of the alloy of the present invention are advantageous because the dynamic strain-hardening effect is associated with the formations of martensites and/or twins, allowing strengthening the material as a function of plastic deformation and avoids localization of strain (i.e. necking) at the early stage of the plastic flow, resulting in an enhanced uniform ductility.

Thus, a first aspect of the invention relates to a beta titanium alloy comprising from 15% to 40% by weight of tungsten; and a balance amount of titanium up to 100% by weight; wherein the alloy comprises from 70% to 100% by volume of an equiaxed beta grain structure. In particular, to a beta titanium alloy comprising from 15% to 28% by weight of tungsten; and a balance amount of titanium up to 100% by weight; wherein the alloy comprises from 70% to 100% by volume of an equiaxed beta grain structure.

The second aspect of the invention relates to a process for the preparation of the beta titanium alloy of the first aspect of the invention which comprises: (a) high temperature melting any of the elements used as raw materials under protective atmosphere, at a temperature from 3000° C. to 3500° C.; (b) cooling down the melted material obtained in step (a) to room temperature to obtain a ingot; (c) thermal treating of the ingot obtained in step (b) at a temperature calculated by the following equation: Tbeta ±100° C.; (d) quenching the alloy obtained in step (c) to room temperature; (e) mechanical working the alloy obtained in step (d) to obtain a worked alloy; (f) thermal treating the worked alloy obtained in step (e) at a temperature calculated by the following equation: Tbeta ±100° C.; and (g) quenching the worked alloy obtained in step (f); wherein Tbeta is as defined below.

And, the third aspect of the invention relates to an implantable medical device made of the beta titanium alloy as defined in the first aspect of the invention.

BRIEF DESCRIPTION OF DRAWINGS

FIG. 1 shows the optical microscopy (OM) images of the microstructure of the titanium tungsten alloy 1 of the present invention. Section A shows the OM images of the alloy 1 having 100% by volume of beta phase at the end of the thermal treating and mechanical working. And, section B shows the OM images of the alloy 1 having about 82.4% by volume of the beta phase transformed during the tensile test to mechanical twins (62.0 vol %) and martensites (20.4 vol %) after deformation.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, any ranges given include both the lower and the upper end-points of the range. Ranges given, such as temperatures, times, percentages of components and the like, should be considered approximate, unless specifically stated.

The term "alloy" refers to a solid solution or liquid mixture of a metal with a second material, said second material may be a metal, a non-metal or another alloy.

For the purpose of the invention, the term "solid solution" refers to a solid form of a solution. The term "solution" refers to a homogeneous mixture composed of two or more substances. In such a mixture, a solute is a substance dissolved in another substance, known as a solvent. The solvent is the larger fraction of the mixture (i.e. titanium) and the remaining components present in the solution other than the solvent are called solutes. In particular, solvents can be gases, liquids or solids. If the solvent is a solid, then the solution is a solid solution wherein gases, liquids and other solids can be dissolved. Therefore, it means that the term "alloy" refers to solid in solid homogeneous mixture. The process for the preparation of a solid solution implies mixing the components in liquid form followed by the subsequent solidification of the resulting mixture.

The terms "balance amount" and "balanced amount" have the same meaning and are used interchangeable. They refer to the sufficient amount of titanium needed for achieving the 100% by weight of the composition.

The term "metastable" refers to a state of pseudoequilibrium of Titanium that has a higher free energy than the true equilibrium state. It means that the alloy is able to accommodate the deformation stress and strain not only by dislocation slip but also by the activation of mechanical twins and martensitic phases.

"The beta phase" of Titanium or Titanium alloys refers to one of the two allotropic forms of titanium having a body-centered cubic structure thermodynamically stable at high temperature (pure titanium 882° C.).

The term "percentage (%) by weight" refers to the percentage of each ingredient of the alloy in relation to the total weight.

The terms "percentage (%) by volume" or "volume/volume %" or "v/v %" or "vol %" have the same meaning and are used interchangeable. They refer to the volume of equiaxed beta grain structure in relation to the total volume of the alloy or the volume of the beta phase transformed during the tensile test to mechanical twins and martensites after deformation.

The term "protective" atmosphere refers to any atmosphere that replaces ambient air. For the purposes of the present invention, a protective atmosphere is an atmosphere that include vacuum or an inert gas such as argon, nitrogen or helium.

The term "quenching" refers to a rapid cooling in a water-based or oil-based solution.

The term "room temperature" refers to a temperature of the environment, without heating or cooling, and is generally comprised from 20° C. to 25° C.

As it is mentioned above, the first aspect of the invention relates to a beta titanium alloy comprising from 15% to 40% by weight of tungsten; and a balance amount of titanium up to 100% by weight; wherein the alloy comprises from 70% to 100% by volume of an equiaxed beta grain structure. In an embodiment, the beta titanium alloy comprises from 15% to 35% by weight of tungsten; and a balance amount of titanium up to 100% by weight; wherein the alloy comprises from 70% to 100% by volume of an equiaxed beta grain structure. In an embodiment, the beta titanium alloy comprising from 15% to 28% by weight of tungsten; and a balance amount of titanium up to 100% by weight; wherein the alloy comprises from 70% to 100% by volume of an equiaxed beta grain structure. In an embodiment, the beta titanium alloy comprises from 18% to 22% by weight of tungsten; and a balance amount of titanium up to 100% by weight; wherein the alloy comprises from 70% to 100% by volume of an equiaxed beta grain structure. The volume fraction of the beta phase can be measured by several methods known in the state of the art such as quantitative X-ray diffraction (XRD) method and by Electron backscatter diffraction (EBSD) method. In the present invention, the measurement of the volume fraction of the beta phase was performed by X-ray diffractogram that comprises 3 characteristic peaks at 38.9, 56.4 and 70.7±0.3 degrees 2 theta at a Cu-K$_\alpha$ radiation, $\lambda$=1.5406 Å, and then the volume fraction of beta phase was quantified by Rietvald refinement. The Rietvald refinement is a commonly used method for the post treatment of X-ray diffraction profile. This method is performed by theoretical simulation of the experimental profile, which provide the quantification of the volume of the alloy which is in beta phase (cf. D. L. Bish et al J. Appl. Cryst. "Quantitative Phase Analysis Using the Rietveld Method", 1988, Vol. 21, pp. 86-91).

In an embodiment, the beta titanium alloy of the invention consists essentially of 15% to 40% by weight of tungsten; and a balance amount of titanium up to 100% by weight; wherein the alloy comprises from 70% to 100% by volume of an equiaxed beta grain structure. In an embodiment, the beta titanium alloy of the invention consists essentially of 15% to 35% by weight of tungsten; and a balance amount of titanium up to 100% by weight; wherein the alloy comprises from 70% to 100% by volume of an equiaxed beta grain structure. In an embodiment, the beta titanium alloy of the invention consists essentially of 15% to 28% by weight of tungsten; and a balance amount of titanium up to 100% by weight; wherein the alloy comprises from 70% to 100% by volume of an equiaxed beta grain structure. In an embodiment, the beta titanium alloy of the invention consists essentially of 18% to 22% by weight of tungsten; and a balance amount of titanium up to 100% by weight; wherein the alloy comprises from 70% to 100% by volume of an equiaxed beta grain structure. As used herein, the term "consisting essentially of" refers to the essential elements of the alloy which are deliberately mixed to form the desired alloy having a desired properties. It should, however, be understood that small amounts of other elements may be part of the alloy as claimed which are not deliberately added but which appear in the final alloy. Thus, such elements may be tolerated without adversely influencing the properties of the alloy. Hence, the presence of such elements in the alloy is deemed to be within the scope of the alloy of the invention.

In an embodiment, the beta titanium alloy of the invention comprises from 80% to 100% by volume of an equiaxed beta grain structure. In an embodiment, the beta titanium alloy of the invention comprises from 90% to 100% by volume of an equiaxed beta grain structure. In an embodiment, the beta titanium alloy of the invention comprises from 95% to 100% by volume of an equiaxed beta grain structure. In an embodiment, the beta titanium alloy of the invention comprises from 98% to 100% by volume of an equiaxed beta grain structure. In an embodiment, the beta titanium alloy of the invention comprises from 99% to 100% by volume of an equiaxed beta grain structure. In an embodiment, the beta titanium alloy of the invention comprises 100% by volume of an equiaxed beta grain structure.

In an embodiment, the beta titanium alloy of the invention is one wherein each grain of the equiaxed beta grain structure has an average diameter from 0.01 µm to 200 µm. In an embodiment, the beta titanium alloy of the invention is one wherein each grain of the equiaxed beta grain structure has an average diameter from 0.01 µm to 180 µm. In an embodiment, the beta titanium alloy of the invention is one wherein each grain of the equiaxed beta grain structure has an average diameter from 0.01 µm to 160 µm. In an embodiment, the beta titanium alloy of the invention is one wherein each grain of the equiaxed beta grain structure has an average diameter from 0.01 µm to 140 µm. In an embodiment, the beta titanium alloy of the invention is one wherein each grain of the equiaxed beta grain structure has an average diameter from 0.5 µm to 120 µm. In an embodiment, the beta titanium alloy of the invention is one wherein each grain of the equiaxed beta grain structure has an average diameter from 2 µm to 90 µm. In an embodiment, the beta titanium alloy of the invention is one wherein each grain of the equiaxed beta grain structure has an average diameter from 5 µm to 70 µm. In an embodiment, the beta titanium alloy of the invention is one wherein each grain of the equiaxed beta grain structure has an average diameter from 8 µm to 60 µm. In an embodiment, the beta titanium alloy of the invention is one wherein each grain of the equiaxed beta grain structure has an average diameter from 10 µm to 50 µm. In an embodiment, the beta titanium alloy of the invention is one wherein each grain of the equiaxed beta grain structure has an average diameter from 12 µm to 40 µm.

The term "average diameter" refers to the size of the equiaxed beta grain measured in µm. The measurement was performed with an appropriate apparatus by conventional analytical techniques such as, for example, microscopic determination utilizing a scanning electron microscope (SEM). In the present invention the average diameter was measured by the Standard Test Methods for Determining Average Grain Size according to ASTM E112.

In an embodiment, the beta titanium alloy of the invention comprises from 18% to 25% by weight of tungsten and balance amount of titanium up to 100% by weight. In an embodiment, the beta titanium alloy of the invention comprises from 20% to 23% by weight of tungsten and balance amount of titanium up to 100% by weight. In an embodiment, the beta titanium alloy of the invention comprises 21% by weight of tungsten and balance amount of titanium up to 100% by weight. In an embodiment, the beta titanium alloy of the invention consists essentially of 21% by weight of tungsten and balance amount of titanium up to 100% by weight.

In an embodiment, the beta titanium alloy of the invention further comprises at least one metal element selected from the group consisting of iridium, tantalum, platinum, gold, iron, niobium, zirconium, tin and molybdenum. In an embodiment, the beta titanium alloy of the invention consists essentially of 15% to 40% by weight of tungsten; at least one metal element selected from the group consisting of iridium, tantalum, platinum, gold, iron, niobium, zirconium, tin and molybdenum; and a balance amount of titanium up to 100% by weight. In an embodiment, the beta titanium alloy of the invention consists essentially of 15% to 35% by weight of tungsten; at least one metal element selected from the group consisting of iridium, tantalum, platinum, gold, iron, niobium, zirconium, tin and molybdenum; and a balance amount of titanium up to 100% by weight. In an embodiment, the beta titanium alloy of the invention consists essentially of 15% to 28% by weight of tungsten; at least one metal element selected from the group consisting of iridium, tantalum, platinum, gold, iron, niobium, zirconium, tin and molybdenum; and a balance amount of titanium up to 100% by weight. In an embodiment, the beta titanium alloy of the invention consists essentially of 18% to 22% by weight of tungsten; at least one metal element selected from the group consisting of iridium, tantalum, platinum, gold, iron, niobium, zirconium, tin and molybdenum; and a balance amount of titanium up to 100% by weight.

In an embodiment, the beta titanium alloy of the invention further comprises at least one metal element selected from the group consisting of iridium, tantalum, platinum, gold, iron, niobium, zirconium, and tin. In an embodiment, the beta titanium alloy of the invention consists essentially of 15% to 40% by weight of tungsten; at least one metal element selected from the group consisting of iridium, tantalum, platinum, gold, iron, niobium, zirconium, and tin; and a balance amount of titanium up to 100% by weight. In an embodiment, the beta titanium alloy of the invention consists essentially of 15% to 35% by weight of tungsten; at least one metal element selected from the group consisting of iridium, tantalum, platinum, gold, iron, niobium, zirconium, and tin; and a balance amount of titanium up to 100% by weight. In an embodiment, the beta titanium alloy of the invention consists essentially of 15% to 28% by weight of tungsten; at least one metal element selected from the group consisting of iridium, tantalum, platinum, gold, iron, niobium, zirconium, and tin; and a balance amount of titanium up to 100% by weight. In an embodiment, the beta titanium alloy of the invention consists essentially of 18% to 22% by weight of tungsten; at least one metal element selected from the group consisting of iridium, tantalum, platinum, gold, iron, niobium, zirconium, and tin; and a balance amount of titanium up to 100% by weight. In an embodiment, the beta titanium alloy of the invention consists essentially of 18% to 22% by weight of tungsten; at least one metal element selected from the group consisting of iridium, tantalum, platinum, gold, iron, niobium, zirconium, and tin; and a balance amount of titanium up to 100% by weight.

In an embodiment, the beta titanium alloy of the invention further comprises iridium.

In an embodiment, the beta titanium alloy of the invention further comprises at least one metal element (M) selected from the group consisting of iridium, tantalum, platinum, gold, iron, niobium, zirconium, tin and molybdenum; wherein the amount of the metal element (Weq weight %) is calculated by the following equation:

$$Weq \text{ weight \%} = \text{substituted amount of tungsten (wt. \%)/equivalence factor } (F)$$

wherein the equivalence factor is as follows:

| Substitution element | Equivalence factor (F) |
|---|---|
| Ir | 1.8 |
| Ta | 0.37 |
| Pt | 0.68 |
| Au | 0.81 |
| Nb | 0.47 |
| Fe | 3.3 |

| Substitution element | Equivalence factor (F) |
| --- | --- |
| Zr | 0.8 |
| Sn | 0.05 |
| Mo | 1.75 |

In an embodiment, when the beta titanium alloy of the invention further comprises from 1 to nine metal elements $M_{1-9}$, then the amount of each metal elements ($y_{1-9}$) and the amount of tungsten (x) is calculated by the following equation:

$$Ti-Weq\% \ W=Ti-x\% \ W-y_1/F_1\% \ M_1-y_2/F_2\% \ M_2-y_3/F_3\% \ M_3-y_4/F_4\% \ M_4-y_5/F_5\% \ M_5-y_6/F_6\% \ M_6-y_7/F_7\% \ M_7-y_8/F_8\% \ M_8-y_9/F_9\% \ M_9$$

wherein:
x is higher than 0,
each $y_{1-9}$ is independently selected from 0 and higher than 0;
$[Weq=x+\Sigma(y_1/F_1+y_2/F_2+y_3/F_3+y_4/F_4+y_5/F_5+y_6/F_6+y_7/F_7+y_8/F_8+y_9/F_9)]$ is comprised from 15 to 40; and
$[x+\Sigma(y_1+y_2+y_3+y_4+y_5+y_6+y_7+y_8+y_9)]$ is comprised from 4.5 and 49.9.

In an embodiment, the beta titanium alloy of the invention further comprises at least one metal element (M) selected from the group consisting of iridium, tantalum, platinum, gold, iron, niobium, zirconium, tin and molybdenum; wherein the amount of the metal element (Weq weight %) is calculated by the following equation:

$Weq$ weight %=substituted amount of tungsten (wt. %)/equivalence factor ($F$)

wherein the equivalence factor is as follows:

| Substitution element | Equivalence factor (F) |
| --- | --- |
| Ir | 1.8 |
| Ta | 0.37 |
| Pt | 0.68 |
| Au | 0.81 |
| Nb | 0.47 |
| Fe | 3.3 |
| Zr | 0.8 |
| Sn | 0.05 |
| Mo | 1.75 |

In an embodiment, when the beta titanium alloy of the invention further comprises from 1 to nine metal elements $M_{1-9}$, then the amount of each metal elements ($y_{1-9}$) and the amount of tungsten (x) is calculated by the following equation:

$$Ti-Weq\% \ W=Ti-x\% \ W-y_1/F_1\% \ M_1-y_2/F_2\% \ M_2-y_3/F_3\% \ M_3-y_4/F_4\% \ M_4-y_5/F_5\% \ M_5-y_6/F_6\% \ M_6-y_7/F_7\% \ M_7-y_8/F_8\% \ M_8-y_9/F_9\% \ M_9$$

wherein:
x is higher than 0,
each $y_{1-9}$ is independently selected from 0 and higher than 0;
$[Weq=x+\Sigma(y_1/F_1+y_2/F_2+y_3/F_3+y_4/F_4+y_5/F_5+y_6/F_6+y_7/F_7+y_8/F_8+y_9/F_9)]$ is comprised from 15 to 40; and
$[x+\Sigma(y_1+y_2+y_3+y_4+y_5+y_6+y_7+y_8+y_9)]$ is comprised from 4.55 and 49.9.
In an embodiment, $[x+\Sigma(y_1/F_1+y_2/F_2+y_3/F_3+y_4/F_4+y_5/F_5+y_6/F_6+y_7/F_7+y_8/F_8+y_9/F_9)]$ is comprised from 15 to 28; and $[x+\Sigma(y_1+y_2+y_3+y_4+y_5+y_6+y_7+y_8+y_9)]$ is comprised from 4.55 and 49.9.

In an embodiment, the beta titanium alloy of the invention further comprises at-least one metal element (M) selected from the group consisting of iridium, tantalum, platinum, gold, iron, niobium, zirconium, and tin; wherein the amount of the metal element (Weq weight %) is calculated by the following equation:

$Weq$ weight %=substituted amount of tungsten (wt. %)/equivalence factor ($F$)

wherein the equivalence factor is as follows:

| Substitution element | Equivalence factor (F) |
| --- | --- |
| Ir | 1.8 |
| Ta | 0.37 |
| Pt | 0.68 |
| Au | 0.81 |
| Nb | 0.47 |
| Fe | 3.3 |
| Zr | 0.8 |
| Sn | 0.05 |

In an embodiment, when the beta titanium alloy of the invention further comprises from 1 to eight metal elements $M_{1-8}$, then the amount of each metal elements ($y_{1-8}$) and the amount of tungsten (x) is calculated by the following equation:

$$Ti-Weq\% \ W=Ti-x\% \ W-y_1/F_1\% \ M_1-y_2/F_2\% \ M_2-y_3/F_3\% \ M_3-y_4/F_4\% \ M_4-y_5/F_5\% \ M_5-y_6/F_6\% \ M_6-y_7/F_7\% \ M_7-y_8/F_8\% \ M_8$$

wherein:
x is higher than 0,
each $y_{1-8}$ is independently selected from 0 and higher than 0;
$[Weq=x+\Sigma(y_1/F_1+y_2/F_2+y_3/F_3+y_4/F_4+y_5/F_5+y_6/F_6+y_7/F_7+y_8/F_8)]$ is comprised from 15 to 40; and
$[x+\Sigma(y_1+y_2+y_3+y_4+y_5+y_6+y_7+y_8)]$ is comprised from 4.5 and 49.9.

In an embodiment, the beta titanium alloy of the invention further comprises at-least one metal element (M) selected from the group consisting of iridium, tantalum, platinum, gold, iron, niobium, zirconium, and tin; wherein the amount of the metal element (Weq weight %) is calculated by the following equation:

$Weq$ weight %=substituted amount of tungsten (wt. %)/equivalence factor ($F$)

wherein the equivalence factor is as follows:

| Substitution element | Equivalence factor (F) |
| --- | --- |
| Ir | 1.8 |
| Ta | 0.37 |
| Pt | 0.68 |
| Au | 0.81 |
| Nb | 0.47 |
| Fe | 3.3 |
| Zr | 0.8 |
| Sn | 0.05 |

In an embodiment, when the beta titanium alloy of the invention further comprises from 1 to eight metal elements $M_{1-8}$, then the amount of each metal elements ($y_{1-8}$) and the amount of tungsten (x) is calculated by the following equation:

$$Ti-Weq\% \ W=Ti-x\% \ W-y_1/F_1\% \ M_1-y_2/F_2\% \ M_2-y_3/F_3\% \ M_3-y_4/F_4\% \ M_4-y_5/F_5\% \ M_5-y_6/F_6\% \ M_6-y_7/F_7\% \ M_7-y_8/F_8\% \ M_8$$

wherein:
x is higher than 0, each $y_{1-8}$ is independently selected from 0 and higher than 0;
[Weq=x+Σ($y_1/F_1+y_2/F_2+y_3/F_3+y_4/F_4+y_5/F_5+y_6/F_6+y_7/F_7+y_8/F_8$)] is comprised from 15 to 40; and
[x+Σ($y_1+y_2+y_3+y_4+y_5+y_6+y_7+y_8$)] is comprised from 4.55 and 49.9.

In an embodiment [x+Σ($y_1/F_1+y_2/F_2+y_3/F_3+y_4/F_4+y_5/F_5+y_6/F_6+y_7/F_7+y_8/F_8$)] is comprised from 15 to 28; and [x+Σ($y_1+y_2+y_3+y_4+y_5+y_6+y_7+y_8$)] is comprised from 4.55 and 49.9.

In an embodiment, the beta titanium alloy of the invention further comprises an amount of iridium comprises from 2% to 4% by weight. In an embodiment, the beta titanium alloy of the invention further comprises an amount of iridium comprises from 3% to 4% by weight. In an embodiment, the beta titanium alloy of the invention further comprises 3.6% by weight of iridium.

In an embodiment, the beta titanium alloy of the invention comprises from 18% to 40% by weight of tungsten, from 2% to 4% by weight of iridium, and balance amount of titanium up to 100% by weight. the beta titanium alloy of the invention comprises from 18% to 35% by weight of tungsten, from 2% to 4% by weight of iridium, and balance amount of titanium up to 100% by weight. In an embodiment, the beta titanium alloy of the invention comprises from 18% to 25% by weight of tungsten, from 2% to 4% by weight of iridium, and balance amount of titanium up to 100% by weight. In an embodiment, the beta titanium alloy of the invention comprises from 18% to 22% by weight of tungsten, from 2% to 4% by weight of iridium, and balance amount of titanium up to 100% by weight. In an embodiment, the beta titanium alloy of the invention comprises from 20% to 23% by weight of tungsten, from 2% to 4% by weight of iridium, and balance amount of titanium up to 100% by weight. In an embodiment, the beta titanium alloy of the invention comprises 21% by weight of tungsten, 3.6% by weight of iridium, and balance amount of titanium up to 100% by weight. In an embodiment, the beta titanium alloy of the invention consists essentially of 21% by weight of tungsten, 3.6% by weight of iridium, and balance amount of titanium up to 100% by weight.

In an embodiment, the beta titanium alloy of the invention, wherein the alloy has a yielding stress comprised from 400 MPa to 1000 MPa. In an embodiment, the beta titanium alloy of the invention, wherein the alloy has a yielding stress comprised from 550 MPa to 900 MPa. In an embodiment, the beta titanium alloy of the invention, wherein the alloy has a yielding stress comprised from 600 MPa to 800 MPa. The terms "yielding stress", "YS", "yield strength" and "yield point" have the same meaning and are used interchangeable. They refer to the stress at which a material begins to deform plastically, that is irreversibly. In other words, it is the maximum stress that can be applied without exceeding a specified value of permanent strain. In the present invention, the "yielding stress" was characterized by uniaxial tensile testing according to ASTM E8/E8M.

In an embodiment, the beta titanium alloy of the invention, wherein the alloy has an ultimate tensile strength comprised from 650 MPa to 1100 MPa. In an embodiment, the beta titanium alloy of the invention, wherein the alloy has an ultimate tensile strength comprised from 700 MPa to 1000 MPa. In an embodiment, the beta titanium alloy of the invention, wherein the alloy has an ultimate tensile strength comprised from 730 MPa to 980 MPa. As used herein the terms "ultimate tensile strength" and "UTS" have the same meaning and are used interchangeable. They refer to the maximum stress a material can withstand before fracture. In the present invention, the UTS was measured by uniaxial tensile testing according to ASTM E8/E8M.

In an embodiment, the beta titanium alloy of the invention, wherein the alloy has an elongation after fracture comprised from 30% to 65%. In an embodiment, the beta titanium alloy of the invention, wherein the alloy has an elongation after fracture comprised from 35% to 60%. The terms "elongation after fracture" and "El" have the same meaning and are used interchangeable. They refer to the percent elongation reported in a tensile test, that is the maximum elongation of the gauge length divided by the original gauge length. In the present invention, the El was measured by the formula (Lu−Lo)/Loχ 100 wherein Lu represents gauge length at fracture and Lo represents original gauge length according to the European EN 10002 standard and ASTM E8M.

In an embodiment, the beta titanium alloy of the invention, wherein the alloy has a Young's modulus comprised from 80 GPa to 140 GPa. In an embodiment, the beta titanium alloy of the invention, wherein the alloy has a Young's modulus comprised from 85 GPa to 130 GPa. The terms "Young's modulus" and "elastic modulus" have the same meaning and are used interchangeable. They refer to the measurement of the stiffness of a solid material. It is a mechanical property of linear elastic solid materials. It defines the relationship between stress (force per unit area) and strain (proportional deformation) in a material. In the present invention, it is measured by uniaxial tensile testing ASTM E8/E8M.

In an embodiment, the beta titanium alloy of the invention wherein the alloy has an average strain-hardening rate from 1000 MPa to 2500 MPa. In an embodiment, the beta titanium alloy of the invention, wherein the alloy has an average strain-hardening rate from 1500 MPa to 2000 MPa. In an embodiment, the beta titanium alloy of the invention, wherein the alloy has an average strain-hardening rate from 1600 MPa to 1800 MPa. The term "average strain hardening rate" and "SHR" have the same meaning and are used interchangeable. They refer to the average speed of the hardening effect as a function of tensile strain: mean(dσ/dε). In the present invention, it was measured from true stress (σ)-true strain (ε) curves by uniaxial tensile testing ASTM E8/E8M.

In an embodiment, the beta titanium alloy of the invention wherein the alloy has one or more of the following properties: a yielding stress comprised from 400 MPa to 1000 MPa; an ultimate tensile strength comprised from 650 MPa to 1100 MPa; an elongation after fracture comprised from 30% to 65%; and a Young's modulus comprised from 80 GPa to 140 GPa.

In an embodiment, the beta titanium alloy of the invention wherein the alloy has a yielding stress comprised from 400 MPa to 1000 MPa; and an ultimate tensile strength comprised from 650 MPa to 1100 MPa. In an embodiment, the beta titanium alloy of the invention wherein the alloy has a yielding stress comprised from 400 MPa to 1000 MPa; and an elongation after fracture comprised from 30% to 65%. In an embodiment, the beta titanium alloy of the invention wherein the alloy has a yielding stress comprised from 400 MPa to 1000 MPa; and a Young's modulus comprised from 80 GPa to 140 GPa. In an embodiment, the beta titanium alloy of the invention wherein the alloy has an ultimate tensile strength comprised from 650 MPa to 1100 MPa; and an elongation after fracture comprised from 30% to 65%. In an embodiment, the beta titanium alloy of the invention wherein the alloy has an elongation after fracture comprised from 30% to 65%; and a Young's modulus comprised from 80 GPa to 140 GPa. In an embodiment, the beta titanium alloy of the invention wherein the alloy has an ultimate tensile strength comprised from 650 MPa to 1100 MPa; and a Young's modulus comprised from 80 GPa to 140 GPa.

In an embodiment, the beta titanium alloy of the invention wherein the alloy has a yielding stress comprised from 400 MPa to 1000 MPa; an ultimate tensile strength comprised from 650 MPa to 1100 MPa; and an elongation after fracture comprised from 30% to 65%. In an embodiment, the beta titanium alloy of the invention wherein the alloy has a yielding stress comprised from 400 MPa to 1000 MPa; an ultimate tensile strength comprised from 650 MPa to 1100 MPa; and a Young's modulus comprised from 80 GPa to 140 GPa. In an embodiment, the beta titanium alloy of the invention wherein the alloy has a yielding stress comprised from 400 MPa to 1000 MPa; an elongation after fracture comprised from 30% to 65%; and a Young's modulus comprised from 80 GPa to 140 GPa. In an embodiment, the beta titanium alloy of the invention wherein the alloy has a yielding stress comprised from 400 MPa to 1000 MPa; an ultimate tensile strength comprised from 650 MPa to 1100 MPa; an elongation after fracture comprised from 30% to 65%; and a Young's modulus comprised from 80 GPa to 140 GPa.

It is noteworthy that the appropriate structure and mechanical features of Titanium and tungsten alloys of the present invention are determined by the chemical composition of the alloy and also by the thermo-mechanical processing of mixture of metals forming the alloy. The beta titanium alloy of the invention may also be defined by its preparation process, thus, it is the one which is obtainable by a process which comprises: (a) high temperature melting any of the elements used as raw materials under protective atmosphere, at a temperature from 3000° C. to 3500° C.; (b) cooling down the melted material obtained in step (a) to room temperature to obtain a ingot; (c) thermal treating of the ingot obtained in step (b) at a temperature calculated by the following equation: Tbeta ±100° C.; (d) quenching the alloy obtained in step (c) to room temperature; (e) mechanical working the alloy obtained in step (d) to obtain a worked alloy; (f) thermal treating the worked alloy obtained in step (e) at a temperature calculated by the following equation: Tbeta ±100° C.; and (g) quenching the worked alloy obtained in step (f); wherein Tbeta is calculated by the following equation:

$$Tbeta = 825 - 6.54 Weq$$

when the alloy further comprises at least one metal element (M) selected from the group consisting of iridium, tantalum, platinum, gold, iron, niobium, zirconium, tin and molybdenum, then the Weq is calculated by the following equation:

$$Ti-Weq\ \%\ W=Ti-x\ \%\ W-y_1/F_1\ \%\ M_1-y_2/F_2\ \%\ M_2-y_3/F_3\ \%\ M_3-y_4/F_4\ \%\ M_4-y_5/F_5\ \%\ M_5-y_6/F_6\ \%\ M_6-y_7/F_7\ \%\ M_7-y_8/F_8\ \%\ M_8-y_9/F_9\ \%\ M_9$$

wherein:
Ti is the amount of Titanium;
x is the amount of tungsten and is higher than 0;
each $M_{1-9}$ is different and corresponds to the metal element selected from iridium, tantalum, platinum, gold, iron, niobium, zirconium, tin and molybdenum;
$y_{1-9}$ is the amount of each metal element $M_{1-9}$ and each $y_{1-9}$ is independently selected from 0 and higher than 0;
$F_{1-9}$ is the equivalence factor as defined above;
$[Weq = x + \Sigma(y_1/F_1 + y_2/F_2 + y_3/F_3 + y_4/F_4 + y_5/F_5 + y_6/F_6 + y_7/F_7 + y_8/F_8 + y_9/F_9)]$ is comprised from 15 to 40; and $[x + \Sigma(y_1 + y_2 + y_3 + y_4 + y_5 + y_6 + y_7 + y_8)]$ is comprised from 4.5 and 49.9; particularly 4.55 and 49.9.

or alternatively; when the alloy further comprises at least one metal element (M) selected from the group consisting of iridium, tantalum, platinum, gold, iron, niobium, zirconium, and tin, then the Weq is calculated by the following equation:

$$Ti-Weq\ \%\ W=Ti-x\ \%\ W-y_1/F_1\ \%\ M_1-y_2/F_2\ \%\ M_2-y_3/F_3\ \%\ M_3-y_4/F_4\ \%\ M_4-y_5/F_5\ \%\ M_5-y_6/F_6\ \%\ M_6-y_7/F_7\ \%\ M_7-y_8/F_8\ \%\ M_8$$

wherein:
Ti is the amount of Titanium;
x is the amount of tungsten and is higher than 0;
each $M_{1-8}$ is different and corresponds to the metal element selected from iridium, tantalum, platinum, gold, iron, niobium, zirconium, and tin;
$y_{1-8}$ is the amount of each metal element $M_{1-8}$ and each $y_{1-8}$ is independently selected from 0 and higher than 0;
$F_{1-8}$ is the equivalence factor as defined in claim 5;
$[Weq = x + \Sigma(y_1/F_1 + y_2/F_2 + y_3/F_3 + y_4/F_4 + y_5/F_5 + y_6/F_6 + y_7/F_7 + y_8/F_8)]$ is comprised from 15 to 28 and
$[x + \Sigma(y_1 + y_2 + y_3 + y_4 + y_5 + y_6 + y_7 + y_8)]$ is comprised from 4.5 and 49.9; particularly 4.55 and 49.9.

The term "obtainable by" is used herein to define each specific alloy of the invention by the process for obtaining it and refers to the product obtainable by any of the corresponding processes disclosed herein. For the purposes of the invention the expressions "obtainable", "obtained" and equivalent expressions are used interchangeably and, in any case, the expression "obtainable" encompasses the expression "obtained".

In an embodiment, the beta titanium alloy of the invention is one which is obtainable by a process wherein the high temperature melting step (a) is achieved by performing a process selected from the group consisting of electrical arc, induction, plasma and electron beam. In an embodiment, the beta titanium alloy of the invention is one which is obtainable by a process wherein step (a) is carried out by electrical arc. As it is mentioned above, this process allows obtained the total meting of all raw materials. Thus, the ingot obtained after step (b) is a homogeneous solid solution.

The term "raw material" refers to those materials used to form the alloy of the present invention. Specifically, raw material is a source of material which provides the components of the alloy. For the propose of the invention, raw materials refers to titanium, tungsten, and the metal elements selected from the group consisting of iridium, tantalum, platinum, gold, iron, niobium, zirconium, tin and molybdenum. In an embodiment, the beta titanium alloy of the invention is one which is obtainable by a process wherein the raw material is not in powder form. In an embodiment, the beta titanium alloy of the invention is one which is obtainable by a process wherein the raw material is non-micronized or non-ground.

The term "mechanical working" refers to physical operations on a material that deform it into a desired shape. The mechanical working includes both cold and hot mechanical workings. Examples of mechanical working appropriate for the present invention includes amongst others bending, cutting, drawing, grinding, hammering, rolling, shaving, twisting, drilling and extruding. In an embodiment, the beta titanium alloy of the invention is one which is obtainable by a process which comprises repeating step (e) until obtaining the desired worked alloy.

In an embodiment, the beta titanium alloy of the invention is one which is obtainable by a process wherein the mechanical working is selected from the group consisting of rolling, drawing, drilling and extruding. In an embodiment, the beta titanium alloy of the invention is one which is obtainable by a process wherein the mechanical working comprising extruding to form bar, wire, tube and plate.

In an embodiment, wherein the beta titanium alloy of the present invention comprises from 15% to 40% by weight of tungsten; and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C. In an embodiment, wherein the beta titanium alloy of the present invention comprises from 15% to 35% by weight of tungsten; and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C. In an embodiment, wherein the beta titanium alloy of the present invention comprises from 15% to 28% by weight of tungsten; and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C. In an embodiment, wherein the beta titanium alloy of the present invention comprises from 18% to 22% by weight of tungsten; and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C.

In an embodiment, wherein the beta titanium alloy of the present invention comprises from 15% to 40% by weight of tungsten, from 2% to 4% by weight of iridium, and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C. In an embodiment, wherein the beta titanium alloy of the present invention comprises from 15% to 35% by weight of tungsten, from 2% to 4% by weight of iridium, and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C. In an embodiment, wherein the beta titanium alloy of the present invention comprises from 18% to 25% by weight of tungsten, from 2% to 4% by weight of iridium, and balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 645° C. to 895° C. In an embodiment, wherein the beta titanium alloy of the present invention comprises from 18% to 22% by weight of tungsten, from 2% to 4% by weight of iridium, and a balance amount of titanium up to 100% by weight; wherein the alloy comprises from 70% to 100% by volume of an equiaxed beta grain structure, then the alloy is obtainable by a process wherein the thermal treating of steps (c) and (f) is carrying out at a temperature comprised from 640° C. to 925° C.

In an embodiment, the beta titanium alloy of the invention is one which is obtainable by the process as defined in the present invention further comprising an additional step (b') of re-melting the ingot obtained in step (b) by repeating the high temperature melting of step (a) and the step (b) from 1 to 5 times. In an embodiment, the beta titanium alloy of the invention is one which is obtainable by the process as defined in the present invention further comprising an additional step (b') of re-melting the ingot obtained in step (b) by repeating the high temperature melting of step (a) and the step (b) from 2 to 4 times.

In an embodiment, the beta titanium alloy of the invention is one which is obtainable by the process as defined in the present invention further comprising an additional step (h) after step (d), or after step (g), or after steps (d) and (g) of drying and polishing the alloy obtained in previous step. In an embodiment, the drying and polishing steps can be carried out following any well-known method of the state of the art. Typically, these steps comprise drying by clean compressed air at room temperature until not being residues in liquid followed by mechanical polishing the resulting alloy by using abrasive mediates for the removal of oxidation layer.

The second aspect of the invention relates to a process for the preparation of the beta titanium alloy of the invention as defined above which comprises: (a) high temperature melting any of the elements used as raw materials under protective atmosphere, at a temperature from 3000° C. to 3500° C.; (b) cooling down the melted material obtained in step (a) to room temperature to obtain a ingot; (c) thermal treating of the ingot obtained in step (b) at a temperature calculated by the following equation: Tbeta ±100° C.; (d) quenching the alloy obtained in step (c) to room temperature; (e) mechanical working the alloy obtained in step (d) to obtain a worked alloy; (f) thermal treating the worked alloy obtained in step (e) at a temperature calculated by the following equation: Tbeta ±100° C.; and (g) quenching the worked alloy obtained in step (f); wherein Tbeta is as defined above.

All the embodiments disclosed above for the beta titanium alloy of the first aspect of the invention characterized by a process, also applies for the process for the preparation of the alloy of the second aspect of the invention.

In an embodiment, step (a) of the process of the invention is performed under protective atmosphere, at a temperature from 3000° C. to 3500° C. for a period of time comprised from 1 minute to 30 minutes; particularly from 5 minutes to 10 minutes.

In an embodiment, step (b) of the process of the invention is performed for a period of time comprised from 2 minutes to 20 minutes; particularly from 5 minutes to 10 minutes.

In an embodiment, steps (c) and (f) of the process of the invention are performed for a period of time comprised from 10 seconds to 1 hour; particularly from 1 minute to 30 minutes.

The third aspect of the invention relates to an implantable medical device made of the beta titanium alloy as defined in the first aspect of the invention. The term "implantable medical device" refers to any type of appliance that is totally or partly introduced, surgically or medically, into a patient's body or by medical intervention into a natural orifice, and which is intended to remain there after the procedure.

In an embodiment, the implantable medical device made of the beta titanium alloy as defined in the present invention is one wherein each grain of the equiaxed beta grain structure has an average diameter from 10 µm to 50 µm. In an embodiment, the implantable medical device made of the beta titanium alloy as defined in the present invention is one wherein each grain of the equiaxed beta grain structure has an average diameter from 12 μm to 40 μm.

In an embodiment, the implantable medical device made of the beta titanium alloy as defined in the first aspect of the invention is an stent. The term "stent" refers to an intravascular prosthesis used for repairing, strengthening or maintaining the inner lumen of the vasculature. In an embodiment, the implantable medical device made of the beta titanium alloy as defined in the first aspect of the invention is a balloon expandable stent. On the balloon expandable stent, the implant is crimped in the distal part of a catheter, onto the top of a balloon. When crimped, the stent presents a small diameter thus ensuring the capacity to be transported until the desired part of patient's vasculature. Once the stent is placed on the desired area, the balloon is pressurized and the stent expanded, exerting force against artery.

In an embodiment, the stent made of the beta titanium alloy as defined in the present invention is one wherein each grain of the equiaxed beta grain structure has an average diameter from 10 μm to 50 μm. In an embodiment, the stent made of the beta titanium alloy as defined in the present invention is one wherein each grain of the equiaxed beta grain structure has an average diameter from 12 μm to 40 μm.

It is also part of the invention a process for the preparation of the implantable medical device made of the beta titanium alloy, particularly a stent. The manufacturing of the stent of the present invention can be achieved by any method known in the state of the art, typically by braiding a wire, by laser cutting of a sheet or by laser tube cutting. Once the shape of the stent has been cut, the stent is cleaned in order to remove the rests of non-desired metal, and also to eliminate the oxide layer formed during laser cutting. The process can include additional thermal treatment of the laser cut part of the stent to improve the mechanical properties of the stent such as for example radial force and breakage resistance amongst others. After the descaling process, typically consisting on submerging the stent in acid solution, the stent is polished. This polishing process can be perfumed by serval methods, for instance with sand blasting, into a tumbler or by electropolishing methods. Finally, passivation treatments of the surface of the stent thus obtained can be done to improve biocompatibility and corrosion resistance of the implant.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

The measurement of the volume of the beta phase was performed by X-ray diffractogram that comprises 3 characteristic peaks at 38.9, 56.4 and 70.7±0.3 degrees 2 theta at a Cu-K$_\alpha$ radiation, $\lambda$=1.5406 Å, and then the volume fraction of beta phase was quantified by Rietvald refinement as defined above.

The measurement of the average diameter of the equiaxed beta grains was performed by the Standard Test Methods for Determining Average Grain Size according to ASTM E112.

The measurement of the volume of the beta phase transformed during the tensile test to mechanical twins and martensites after deformation was performed by transmission electron microscope (TEM). 3 mm diameter disks were discharged from the samples after tensile tests. The disks were carefully reduced in thickness first by mechanical polishing to 150 m then by electrochemical polishing to about 100 nm. The bright field (BF) imaging, dark field (DF) imaging and selected area electron diffraction (SEAD) were performed to qualitatively identify the locations and types of deformation products (twins and martensites). Then automated crystal orientation mapping (ACOM) was performed on several zones to quantify the fractions of each deformation products.

1. Alloy Composition

The qualitative and quantitative composition of the alloys of the present invention (cf. Alloy 1 and 2) is disclosed as follows:

| | Chemical composition (% by weight) | | |
|---|---|---|---|
| Alloy | Tungsten (W) | Iridium (Ir) | Titanium (Ti) |
| Alloy 1 | 21 | — | Balanced weight |
| Alloy 2 | 21 | 3.6 | Balanced weight |

2. Process for the Preparation

The process for the preparation of the alloys of the present invention is as follows:

2.1. Alloy 1

A. Starting Materials

Pure (+99.6%) titanium plates in annealed state (commercially available by Goodfellow).

Pure (99.95%) tungsten plates in rolled state (commercially available by Goodfellow).

B. Elaboration

Preparation of the Ingot

Raw plates were cut into square pieces by disk cutting machine and the as-cut pieces were weighted individually. The square pieces thus obtained were cleaned with ethanol and acetone and then dried by clean compressed air.

The cleaned pieces were sealed in the high temperature melting furnace having a chamber with copper crucible. Particularly, the cleaned pieces were placed in the copper crucible, then the camber was sealed to be isolated from atmosphere. The atmosphere of the melting chamber was purged by pure argon for 5 times and then fulfilled by pure argon. Before heating the raw pieces, a Ti—Zr ingot was re-melted to catch residual impurity elements in the furnace atmosphere.

All the raw pieces were melted and mixed at 3000-3500° C. at liquid state, finished by forming a single Ti—W ingot. The Ti—W ingot thus obtained was cooled down in the furnace under argon atmosphere to room temperature. The ingot was turned upside down in the furnace to be re-melted again at 3000-3500° C. The ingot turning-over and re-melting were repeated for 3 times.

Thermal Treating and Mechanical Working

The obtained Ti—W ingot was hanged in vertical tubular furnace. The furnace was sealed and pumped to $10^{-5}$ mbar pressure (vacuum) and the ingot was heated up to 850° C. and annealed at this temperatures for 30 minutes.

At the end of the 30 minutes, the ingot was released and quenched into a tank containing water at room temperature. The quenched ingot was mechanical polished to remove surface oxidation from quenching. The ingot was then cleaned with acetone and ethanol and dried by clean compressed air.

The clean ingot was rolled in rolling machine at room temperature. The rolling step was started from the ingot thickness and repeated at the same direction by progressively reducing the distance between the two rollers. The rolling step was finished at the thickness reduction rate of 95% (thickness reduction rate=(start thickness−finish thickness)/start thickness).

The as-rolled Ti—W sheet was cleaned and hanged in vertical quenching furnace under vacuum at $10^{-5}$ mbar. The sheet was heated up to 850° C. and annealed for 15 minutes at this temperature. The Ti—W sheet was released at the end of the 15 minutes and quenched into a tank with water at room temperature. The quenched Ti—W sheet was mechanical polished and then cleaned and dried to obtain the final sheet made of alloy 1 of the present invention.

2.2. Alloy 2

A. Starting Materials

Pure (+99.6%) titanium plates in annealed state (commercially available by Goodfellow).

Pure (99.95%) tungsten plates in rolled state (commercially available by Goodfellow).

Pure (99.90%) iridium rods in drawn state (commercially available by Goodfellow).

B. Elaboration

Preparation of the Ingot

The process for the preparation of the ingot of Ti—W—Ir is the same as disclosed for alloy 1 using as starting material the raw plates of titanium and tungsten cutted into square pieces by disk cutting machine and the raw rods of iridium cutted into short cylinders by disk cutting machine.

Thermal Treating and Mechanical Working

The process for the preparation of a final sheet made of alloy 2 of the present invention is the same as disclosed for alloy 2 using as starting ingot the ingot of Ti—W—Ir instead of the ingot of Ti—W.

3. Mechanical Properties

A. Tensile Test Method

Tensile specimens with dimensions according to ASTM E8M were machined from the alloys of the present invention obtained in section 2.1 and 2.2.

Tensile test protocol was conforming to ASTM E8/E8M standard for test methods for tension testing of metallic materials.

The long axis of the tensile specimens were parallel to the rolling direction.

The specimens were fixed on Instron tensile machine by using mechanical wedge action grips.

The stress of the fixation were monitored and compensated automatically by tensile test instrument (Instron 5966 with 10 kN force detector) during the specimen fixation to avoid pre-charge.

High precision strain extensometer (Instron 2630-102, +/−50% max strain) was attached to the center of the gauge for deformation measurement.

Deformation speed was fixed to $10^{-3}$ $S^{-1}$.

Several specimens were tested under the same condition, then the tensile curves were treated by Bluehill software for final results.

B. Results

The tensile test results were summarized in the following Table:

| Mechanical properties | Alloy 1 | Alloy 2 |
|---|---|---|
| Yielding stress (YS) | 600 MPa | 783 MPa |
| Ultimate tensile strength (UTS) | 730 MPa | 972 MPa |
| Elongation after fracture (El) | 55% | 37% |
| Young's modulus | 90 GPa | 124 GPa |
| Average strain-hardening rate | 1600 MPa | 1780 MPa |
| UTS-YS | 130 MPa | 189 MPa |

As it is shown in the tensile test results, the alloys of the invention have the appropriate chemical composition and mechanical properties for the preparation of implantable medical device, which should have a yielding stress comprised from 400 MPa to 1000 MPa and a elongation after fracture comprised from 30% to 65%.

4. Phase and Microstructure

A. Method

Specimens:

Alloy obtained after the thermal treating and mechanical working.

Alloy obtained after tensile test.

Method:

Specimens were mechanical polished to mirror-like finishing and then the polished surface was immerged into Kroll's reagent (a mixture of HF, $HNO_3$ and $H_2O$) at room temperature for 1 minute. Polished specimens were cleaned by water and ethanol then dried by compressed air. Optical microscopy images were taken before and after tensile deformation at the etched surface.

The optical microscopy images were taken by an Olympus PME metallography microscope with CCD camera.

B. Results

Alloy 1

Alloy 1 has 100% by volume of beta phase at the end of the thermal treating and mechanical working formed in equiaxial grains having an average diameter of about 122 m (cf. FIG. 1A). Nevertheless, about 82% by volume of beta phase was strain-transformable during tensile test to mechanical twins and martensites after deformation (cf. FIG. 1B).

Alloy 2

Alloy 2 has about 95% by volume of beta phase at the end of the thermal treating and mechanical working formed in equiaxial grains having an average diameter of about 65 m with dispersed fine precipitates in beta grains and at grain boundaries. Nevertheless, about 80% by volume of beta phase was strain-transformable during tensile test to mechanical twins and martensites after deformation.

CITATION LIST

1. Standard Test Methods for Determining Average Grain Size according to ASTM E112
2. Standard Test Methods according to ASTM E8/E8M
3. European EN 10002 standard ASTM E8M
4. D. L. Bish et al J. Appl. Cryst. "Quantitative Phase Analysis Using the Rietveld Method", 1988, Vol. 21, pp. 86-91)

For reasons of completeness, various aspects of the invention are set out in the following numbered clauses:

Clause 1. A beta titanium alloy comprising from 15% to 28% by weight of tungsten; and a balance amount of titanium up to 100% by weight; wherein the alloy comprises from 70% to 100% by volume of an equiaxed beta grain structure.

Clause 2. The beta titanium alloy according to clause 1, which comprises 100% by volume of the equiaxed beta grain structure.

Clause 3. The beta titanium alloy according to any of the clauses 1-2, wherein each beta grain of the equiaxed beta grain structure has an average diameter from 0.01 μm to 200 μm.

Clause 4. The beta titanium alloy according to any of the clauses 1-3, wherein the alloy further comprises at least one metal element selected from the group consisting of iridium, tantalum, platinum, gold, iron, niobium, zirconium, and tin.

Clause 5. The beta titanium alloy according to clause 4, wherein the amount of the metal element (W-eq) is calculated by the following equation:

$$W\text{-}eq \text{ weight \%} = \text{substituted amount of tungsten (wt. \%)/equivalence factor } (F)$$

wherein the equivalence factor is as follows:

| Substitution element | Equivalence factor (F) |
| --- | --- |
| Ir | 1.8 |
| Ta | 0.37 |
| Pt | 0.68 |
| Au | 0.81 |
| Nb | 0.47 |
| Fe | 3.3 |
| Zr | 0.8 |
| Sn | 0.05 |

Clause 6. The beta titanium alloy according to any of the clauses 1-5, wherein the alloy comprises from 18% to 22% by weight of tungsten.

Clause 7. The beta titanium alloy according to any of the clauses 1-6, wherein the alloy comprises from 2% to 4% by weight of iridium.

Clause 8. The beta titanium alloy according to any of the clauses 1-7, wherein the alloy has one or more of the following properties:
  a yielding stress comprised from 400 MPa to 1000 MPa;
  an ultimate tensile strength comprised from 650 MPa to 1100 MPa;
  an elongation after fracture comprised from 30% to 65%; and
  a Young's modulus comprised from 80 GPa to 140 GPa.

Clause 9. The beta titanium alloy according to any of the clauses 1-8, which is obtainable by a process which comprises:
  (a) high temperature melting any of the elements used as raw materials under protective atmosphere, at a temperature from 3000° C. to 3500° C.;
  (b) cooling down the melted material obtained in step (a) to room temperature to obtain a ingot;
  (c) thermal treating of the ingot obtained in step (b) at a temperature calculated by the following equation: Tbeta ±100° C.;
  (d) quenching the alloy obtained in step (c) to room temperature;
  (e) mechanical working the alloy obtained in step (d) to obtain a worked alloy;
  (f) thermal treating the worked alloy obtained in step (e) at a temperature calculated by the following equation: Tbeta ±100° C.; and
  (g) quenching the worked alloy obtained in step (f) to room temperature;

wherein Tbeta is calculated by the following equation:

$$T\text{beta} = 825 - 6.54 W_{eq}$$

being Weq calculated by the following equation:

$$\text{Ti-}x\ \%\ W\text{-}y_1/F_1\ \%\ M_1\text{-}y_2/F_2\ \%\ M_2\text{-}y_3/F_3\ \%\ M_3\text{-}y_4/F_4\ \%\ M_4\text{-}y_5/F_5\ \%\ M_5\text{-}y_6/F_6\ \%\ M_6\text{-}y_7/F_7\ \%\ M_7\text{-}y_8/F_8\ \%\ M_8$$

wherein:
  Ti is the amount of Titanium;
  x is the amount of tungsten and is higher than 0;
  each $M_{1-8}$ is different and corresponds to the metal element selected from iridium, tantalum, platinum, gold, iron, niobium, zirconium, and tin;
  $y_{1-8}$ is the amount of each metal element $M_{1-8}$ and each $y_{1-8}$ is independently selected from 0 and higher than 0;
  $F_{1-8}$ is the equivalence factor as defined in clause 5;
  $[x+\Sigma(y_1/F_1+y_2/F_2+y_3/F_3+y_4/F_4+y_5/F_5+y_6/F_6+y_7/F_7+y_8/F_8)]$ is comprised from 15 to 28; and
  $[x+\Sigma(y_1+y_2+y_3+y_4+y_5+y_6+y_7+y_8)]$ is comprised from 4.55 and 49.9.

Clause 10. The beta titanium alloy according to clause 9, wherein the process further comprises an additional step (b') of re-melting the ingot obtained in step (b) by repeating the high temperature melting of step (a) and the step (b) from 1 to 5 times.

Clause 11. The beta titanium alloy according to any of the clauses 9-10, wherein the process further comprises an additional step (h) after step (d), or after step (g), or after steps (d) and (g) of drying and polishing the alloy obtained in respectively previous step.

Clause 12. A process for the preparation of the beta titanium alloy as defined in any of the clauses 1-11, which comprises:
  (a) high temperature melting any of the elements used as raw materials under protective atmosphere, at a temperature from 3000° C. to 3500° C.;
  (b) cooling down the melted material obtained in step (a) to room temperature to obtain a ingot;
  (c) thermal treating of the ingot obtained in step (b) at a temperature calculated by the following equation: Tbeta ±100° C.;
  (d) quenching the alloy obtained in step (c) to room temperature;
  (e) mechanical working the alloy obtained in step (d) to obtain a worked alloy; (f) thermal treating the worked alloy obtained in step (e) at a temperature calculated by the following equation: Tbeta ±100° C.; and
  (g) quenching the worked alloy obtained in step (f);
  wherein Tbeta is as defined in clause 9.

Clause 13. An implantable medical device made of the beta titanium alloy as defined in any of the clauses 1-11.

Clause 14. The implantable medical device according to clause 13, which is a stent.

Clause 15. The implantable medical device according to clause 14, which is a balloon expandable stent.

The invention claimed is:
1. A beta titanium alloy comprising from 15% to 40% by weight of tungsten; and a balance amount of titanium up to 100% by weight:
  wherein the alloy comprises from 70% to 100% by volume of an equiaxed beta grain structure, wherein the alloy is strain transformable, and wherein "strain transformable" means the alloy shows strain-transforming effects when the beta phase is in metastable state as a result of being quenched from beta region T around beta transus temperature;

wherein the beta titanium alloy is obtainable by a process which comprises:
(a) high temperature melting any of the elements used as raw materials under protective atmosphere, at a temperature from 3000° C. to 3500° C.;
(b) cooling down the melted material obtained in step (a) to room temperature to obtain a ingot;
(c) thermal treating of the ingot obtained in step (b) at a temperature calculated by the following equation: Tbeta 100° C.;
(d) quenching the alloy obtained in step (c) to room temperature;
(e) mechanical working the alloy obtained in step (d) to obtain a worked alloy;
(f) thermal treating the worked alloy obtained in step (e) at a temperature calculated by the following equation: Tbeta ±100° C.; and
(g) quenching the worked alloy obtained in step (f) to room temperature;
wherein Tbeta is calculated by the following equation:

$Tbeta=825-6.54Weq$ being Weq calculated by the following equation:

$Ti-Weq\% \ W=Ti-x\% \ W-y_1/F_1\% \ M-y_2/F_2\% \ M_2-y_3/F_3\% \ M_3-y_4/F_4\% \ M_4-y_5/F_5\% \ M_5-y_6/F_6\% \ M_6-y_7/F_7\% \ M_7-y_8/F_8\% \ M_8-y_9/F_9\% \ M_9$ wherein:
Ti is the amount of Titanium;
x is the amount of tungsten and is higher than 0;
each $M_{1-9}$ is different and corresponds to the metal element selected from iridium, tantalum, platinum, gold, iron, niobium, zirconium, tin and molybdenum;
$y_{1-9}$ is the amount of each metal element $M_{1-9}$ and each $y_{1-9}$ is independently selected from 0 and higher than 0;
$F_{1-9}$ is the equivalence factor of the metal element
$[Weq=x+\Sigma(y_1/F_1+y_2/F_2+y_3/F_3+y_4/F_4+y_5/F_5+y_6/F_6+y_7/F_7+y_8/F_8+y_9/F_9)]$ is comprised from 15 to 40; and
$[x+\Sigma(y_1+y_2+y_3+y_4+y_5+y_6+y_7+y_8+y_9)]$ is comprised from 4.5 and 49.9.

2. The beta titanium alloy according to claim 1, wherein the process further comprises an additional step (b') of re-melting the ingot obtained in step (b) by repeating the high temperature melting of step (a) and the step (b) from 1 to 5 times.

3. The beta titanium alloy according to claim 1, wherein the process further comprises an additional step (h) after step (d), or after step (g), or after steps (d) and (g) of drying and polishing the alloy obtained in the previous step, respectively.

* * * * *